(12) United States Patent
Fisher et al.

(10) Patent No.: US 6,183,256 B1
(45) Date of Patent: Feb. 6, 2001

(54) DENTAL CROWN

(76) Inventors: Tommie W. Fisher, 7910 SE. 31$^{st}$ Ave., Portland, OR (US) 97202; Verlin L. Stimpson, 1041 SW. Falcon, Portland, OR (US) 97219; Thomas E. Brumet, 17101 SE. Sager Rd., Portland, OR (US) 97236

( * ) Notice: Under 35 U.S.C. 154(b), the term of this patent shall be extended for 0 days.

(21) Appl. No.: 09/416,409

(22) Filed: Oct. 12, 1999

(51) Int. Cl.$^7$ ...................................................... A61C 5/08
(52) U.S. Cl. ............................................. 433/219; 433/218
(58) Field of Search ..................... 433/218, 219, 433/228.1, 202.1, 222.1, 217

(56) References Cited

U.S. PATENT DOCUMENTS

| | | |
|---|---|---|
| 2,196,505 * | 4/1940 | Morton .............................. 433/219 X |
| 2,537,142 * | 1/1951 | Lankford et al. ................. 433/219 X |
| 3,793,728 * | 2/1974 | Corbineau ......................... 433/219 X |
| 4,398,887 * | 8/1983 | Balde et al. ........................... 433/218 |
| 4,523,912 | 6/1985 | Breustedt et al. . |
| 4,813,874 | 3/1989 | Jensen . |
| 4,834,656 * | 5/1989 | Loudon ............................. 433/218 X |
| 4,877,402 | 10/1989 | Hirabayashi et al. . |
| 4,988,362 | 1/1991 | Toriyama et al. . |
| 5,009,597 | 4/1991 | Schaefer . |
| 5,080,589 | 1/1992 | Oden et al. . |
| 5,250,352 | 10/1993 | Tyszblat . |
| 5,346,717 | 9/1994 | McCrory . |
| 5,360,340 | 11/1994 | Rheinberger et al. . |

* cited by examiner

*Primary Examiner*—Nicholas D. Lucchesi
(74) *Attorney, Agent, or Firm*—Kolisch Hartwell Dickinson McCormack & Heuser

(57) ABSTRACT

A dental prosthetic device, such as a crown or a bridge, which includes a ceramic core that is effectively joined by "cementing" to the stump in a tooth preparation, and a polyceramic outer jacket which is effectively joined by "bonding" to the core.

18 Claims, 1 Drawing Sheet

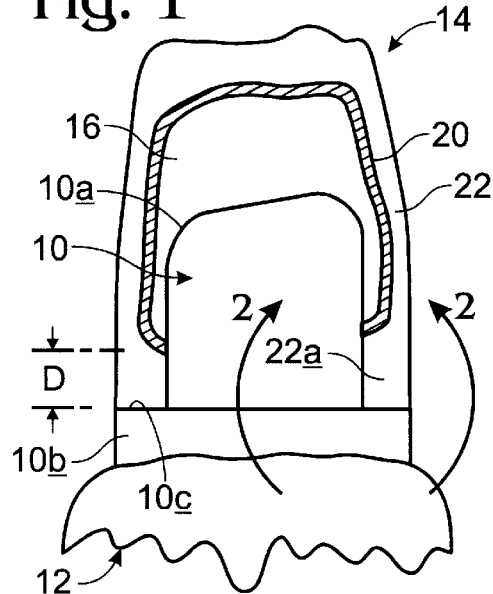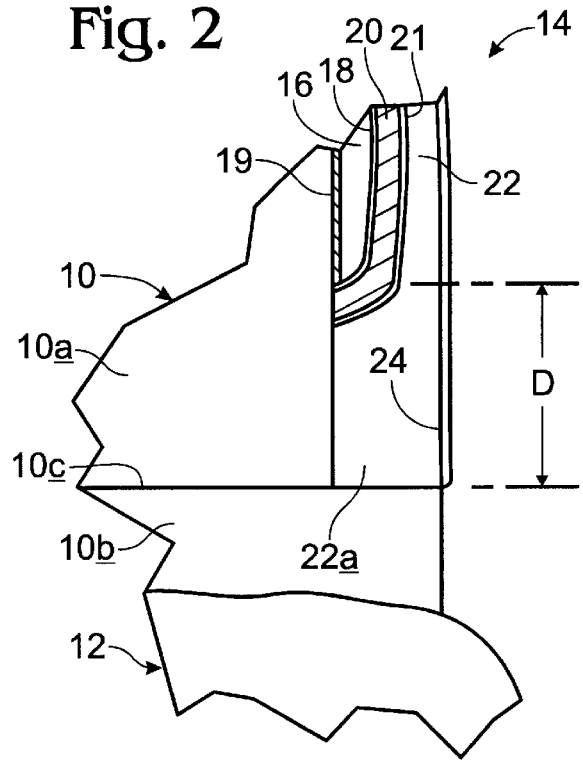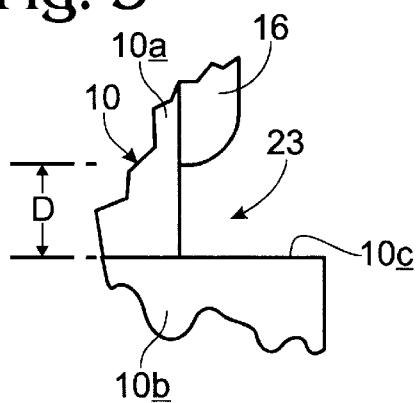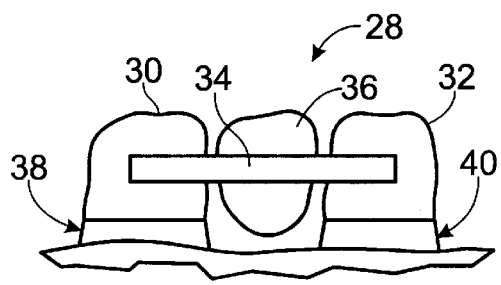

DENTAL CROWN

CROSS-REFERENCE TO RELATED APPLICATION(S)

This application claims priority to Provisional patent application Ser. No. 60/149,021 filed Aug. 13, 1999 titled "Dental Crown".

BACKGROUND AND SUMMARY OF THE INVENTION

The present invention relates to a dental prosthetic device, and very specifically to a new form of dental crown, dental bridge, or like device. In relation to the disclosure herein of this invention, we use two specific terms regarding joinder—"cementing" and "bonding"—which terms are presented throughout the specification within quotation marks to indicate that they have specific meanings employed and understood conventionally in the dental art to describe two, generically different joinery mechanisms. The "cooperative" presence, usability and use of both of these mechanisms, according to the present invention, define advances in the art that are offered specifically by this invention. Also offered by the present invention are a prosthetic device and an installation practice which attend well to matters of aesthetics—i.e., final, in-place "appearance".

For the purpose of principal illustration herein, most of the discussion below is provided in relation to the structure and mounting of a dental crown. Reference to a dental crown is intended to include reference to a dental bridge, as well as to other like structures.

In the dental-crown-related prior art which is associated with this invention, there are fundamentally two different and relatively widely used predecessor crown structures and installation practices. Both have benefits and drawbacks. It is with regard to addressing and eliminating these drawbacks, while preserving and actually enhancing the benefits, that the present invention makes an important contribution to the dental art.

One prior art practice and structure involves preparing a crown which is formed with an aluminum oxide core (the part that seats, effectively, directly against a tooth preparation), and an overlying, outer porcelain jacket. Reference here to aluminum oxide, as well as later references herein to the same material, relate(s) to a conventionally available high-temperature ceramic material which includes aluminum oxide blended with one or more conventional sintering/binder material(s). This kind of crown, after it is built and properly shaped, is typically fitted onto a patient's tooth preparation and secured there by "cementing" it in place. This approach is fairly inexpensive in relation both to the cost of the crown unit per se, and to the specific installation procedure (the installation time required of a dentist). However, there is a recognized drawback which involves the durability of the joint interface that exists between such a crown and a tooth preparation, i.e., the interface between the tooth preparation and the aluminum oxide (or other) core. Apparently, it is very typical that the aluminum oxide core does not produce a good closure seal with a tooth surface, and this jeopardizes crown longevity in the mouth.

The other main prior art approach, one that is called an indirect approach, offers an installation that is considerably more robust in terms of longevity, but one that has the drawback that it is considerably more expensive in the context of installation. This approach involves the forming of a polyceramic crown directly onto a model of a tooth preparation without there being any intermediary aluminum oxide (or other) core. Once formed, the prepared crown is removed from the model for installation on the "natural" tooth preparation—i.e., directly into the mouth of the patient in a dentist's office. There, the polyceramic material in the crown is typically joined to the patient's tooth-preparation surface through a quite time-consuming technique referred to as "bonding" (as distinguished from "cementing"). This kind of crown and related installation, which works very well from a long-life sealing-to-a-tooth-preparation point of view, involves relatively high costs in relation to the typical, relatively long, dental-office "bonding" procedure, wherein a professional dentist's time (substantial time) is required.

It is to address the important issues of good bonding-longevity and overall low cost that the present invention focuses particular attention. As will become apparent, and as also was mentioned above, the invention additionally directs attention to the important matter of "in-place" aesthetics.

According to the invention, a multi-element dental prosthetic device is prepared (for example, a crown) which includes a high-temperature ceramic (preferably aluminum oxide) core, an outer polyceramic jacket, and a plural-layer intermediate layer structure which allows and promotes secure and economically achieved joinder effectively between the core and the jacket. This intermediate layer structure includes a porcelain layer next to the core, a layer of material known in the art as silane next to the porcelain layer, and a layer of a suitable conventional "bonding" material in between the silane layer and the outer jacket. While aluminum oxide is currently preferred as the core material, we recognize that many other kinds of high-temperature ceramic materials may be used. For example, one could employ a composite zirconium material to form the core.

The three-layer intermediate layer structure sets the stage, so-to-speak, and enables what can be considered to be the practical "bonding" of the polyceramic jacket to the ceramic core. This "bonding" condition, which is offered uniquely by the present invention, permits (a) the use of ceramic material as a core which can be joined by "cementing" to a tooth preparation, and (b) the use of polyceramic material in the jacket which most desirably "faces the outside world". In a manner of speaking, the mentioned silane intermediary layer plays a special role in permitting what is referred to herein as the effective joinder by "bonding" of the core and jacket. Silane acts as the linkage broker between the porcelain intermediary layer which anchors well to the ceramic core, and the "bonding"—material intermediary layer which anchors well to the polyceramic jacket. Absent the silane layer in this cooperative trio, the porcelain layer and the "bonding"—material layer would not affix to one another particularly well. Also, the "bonding"—material layer would not anchor well directly with the core material.

Our aluminum oxide core is formed in much the same manner as are currently used aluminum oxide cores, except that this new core is intentionally prepared to have certain outside dimensions that are determinedly reduced in relation to what they would most usually be in a conventional crown. In particular, our aluminum oxide core is appreciably smaller in height in relation to conventional aluminum oxide cores in order to expose an endless, somewhat annular, and generally channel-like region below the core for receiving an inwardly turned rim portion (or lower extremity portion) of the overlying, outer polyceramic jacket. In a final installation, this rim portion makes substantially direct contact with the stump and the associated shoulder in a tooth preparation, and this polyceramic-to-tooth (stump and shoulder) contact enables an especially good seal with a tooth preparation. Good "sealing", in turn, promotes long-life performance.

In the context of a dental crown device prepared in accordance with the present invention, the structural organization of this crown can be viewed, so-to-speak, from several different points of view.

From one point of view, the crown includes fundamentally two main components: (1) an inner, central, high-temperature, ceramic-material (preferably aluminum oxide) core that is directly joinable through "cementing" to the outside of the stump in a tooth preparation; and (2), an outer exposed jacket formed of a suitable polyceramic material, and joined, effectively, through "bonding" to the core.

From another point of view, the device built in accordance with this invention includes three principal components: (1) an inner, central, high-temperature, ceramic-material (preferably aluminum oxide) core that is directly joinable through "cementing" to the outside of the stump in a tooth preparation; (2) a thin, intermediary layer structure, including silane, which promotes "bonding" joinder between the core and a polyceramic jacket; and (3) an outer exposed jacket formed of a suitable polyceramic material joined by "bonding" to the core via the silane-containing, intermediary layer structure.

From yet another point of view, and without necessitating any specific reference to particular materials, the device of this invention includes: (1) a core element that is substantially directly joinable by "cementing" to the outside surface of the stump in a tooth preparation, with the lower extremity of this core element, when it is in place on a preparation stump, terminating short of the region where the stump and the shoulder in the tooth preparation join; and (2) an outer, jacketing wear material which is formed on (and joined effectively by "bonding" to) the outside of the core element, and which includes a lower extremity that, when in place on a tooth preparation, extends fully to the preparation shoulder just mentioned. This just-mentioned lower extremity of the jacketing material includes the inwardly turned rim portion discussed above, which rim portion extends inwardly toward the lower part of the outside surface of the tooth preparation stump, i.e., in a location beneath the lower extremity of the core element.

DESCRIPTION OF THE DRAWING FIGURES

FIG. 1 is a larger-than-natural-size-scale fragmentary view, partly in cross section, illustrating a crown constructed in accordance with the present invention installed and in place on a "natural" tooth preparation.

FIG. 2 is an even larger-scale fragmentary view, also partially in cross section, showing details of the installed in situ structure and of the joinery interfaces regarding the crown and tooth-preparation pictured in FIG. 1.

FIG. 3 is a somewhat simplified view which is much like the view presented in FIG. 2. It differs in that it eliminates certain organizational details depicted in FIG. 2 in order to focus attention on a channel which exists in the region of proximity of (a) a shoulder and stump in the illustrated tooth preparation, and (b) the lower extremity portion of a core component in the invention.

FIG. 4 is a smaller-scale, fragmentary illustration of a dental bridge (in place) including structure formed in accordance with the present invention.

DETAILED DESCRIPTION OF, AND BEST MODE FOR CARRYING OUT, THE INVENTION

FIGS. 1, 2 and 3 illustrate the construction of a crown built in accordance with the present invention. Considering these three figures together, indicated generally at 10 is a tooth preparation including a stump 10a which joins a base 10b through a laterally-outwardly-extending shoulder 10c. In particular, shoulder 10c extends between the outside surface of base 10b and the outside surface of the lower portion of stump 10a. Preparation 10 is seen in these figures to rise above the adjacent gum pictured at 12 in FIGS. 1 and 2. This kind of tooth preparation is conventional, and specifically is one all of whose components are formed from natural tooth material. Other kinds of "tooth preparations" can also be used. Such other preparations can, for example, include settings involving a non-natural root filler in a natural tooth, and an implant device.

Shown at 14 is a crown produced in accordance with the present invention. This crown includes a high-temperature ceramic, aluminum oxide core (or core unit) 16, and immediately on the outside of this core, an important fire-hardened thin intermediary layer of porcelain 18 (FIG. 2). Core 16 is "cemented" to stump 10a through a layer 19 (FIG. 2) of a suitable conventional "cementing" material. A "cementing" material which we have found to be entirely satisfactory is a product known as Panavia 21®. Panavia 21® is a material made by Kuraray Co. Ltd. of Osaka, Japan.

On the outside of porcelain layer 18 is another important intermediary layer 20 formed of silane, and on the outside of layer 20 is a light-cured, thin, intermediary layer 21 (FIG. 2) of a conventional "bonding" material (such as the product made by Jeneric/Pentron called "BOND 1"). An outer polyceramic jacket 22 is "bonded" to the core through layers 21, 20, 18. Core 16, along with layers 18, 20, 21, constitute what is referred to collectively herein as joinder structure. Layers 18, 20, 21 are referred to herein collectively as intermediary layer structure. They (layers 18, 20, 21) play, cooperatively, a key role is joining core 16 to the still-to-be-described outer polyceramic jacket 22, and they thus play an important part in permitting the novel device of the present invention to be joined to a tooth preparation by "cementing", and yet to present a very desirable outside structure of polyceramic material to the "outside world". Additionally, and as will be discussed shortly, they promote the usability of a dental prosthetic structure which is characterized, by virtue of the use of polyceramic material on the outside, by excellent sealing contact with the surface of a tooth preparation.

Jacket 22 is formed of any suitable polyceramic material, such as one which preferably includes a blend of dental-grade, functional, oligocarbonate, dimethacrylic esters, along with appropriate pigments and a silica filler. There are other, known types of usable polyceramic materials that can be employed as well. Significantly, the lower extremity portion of jacket 22 includes the previously mentioned inwardly turned rim portion, shown in FIGS. 1 and 2 at 22a, which effectively seats against and seals both to the base 10b of stump 10a, and to shoulder 10c. More will be said about this shortly.

Formed on the outside of the polyceramic jacket is an appropriate thin layer of various available mixtures of methacraglates with acetones and light curing activators to form a conventional glaze shown at 24 in FIG. 2.

Describing the manner in which crown 14 is prepared, such preparation begins with the creation of an appropriate aluminum oxide core which is designed to fit by "cementing" directly onto the upper portion of a stump in a tooth preparation. This core is prepared in such a fashion that, when it is mounted in place on the stump in a tooth preparation, its bottom extremity does not extend to the region where the stump and the shoulder in the preparation join one another. Typically, there is a vertical gap here which is preferably about 0.5-millimeters. This dimension (exaggerated) is indicated at D in FIGS. 1, 2 and 3. Because of the presence of this gap, the underside of the lower extremity portion of core 16, together with shoulder 10c and the lower exposed portion of stump 10a, define an endless, generally annular channel 23 (see particularly FIG. 3) which circumsurrounds the stump. This channel, whose presence is created by the intentional foreshortening of the overall height of core 16, creates an important structural region wherein jacket 22 can join with and seal to two distinct surface areas on tooth preparation 10. The channel's presence (according to the present invention) thus aids in addressing the "joint interface" integrity issue discussed earlier.

After preparation of the core material, the outside core-material surface receives, as by brushing, a thin, intermediary layer of a suitable flowable porcelain material which is then appropriately fired to hardness.

The hardened porcelain layer is next treated, as by sand-blasting or acid etching, to roughen it so as to provide a good reception surface for the next material to be formed in accordance with the invention.

Onto this roughened outside surface of the thin porcelain layer there is suitably applied a thin coating of liquid silane which, after application, is blown dry. This silane layer promotes significantly good and tenacious, effective "bonding" between the core and the jacket through anchoring especially well both to the porcelain intermediary layer, and to the still-to-be-applied "bonding" adhesive intermediary layer.

Next, appropriately formed on the outside surface of the silane layer is a coating (intermediary layer) of a conventional liquid primer "bonding" adhesive, such as the product known as "BOND 1" made by Jeneric/Pentron in Wallingford, Conn. This coating is next conventionally light cured in a pressurized, nitrogen-rich chamber.

Following preparations of the silane and adhesive-material coatings or layers, and typically performed in several "build-up" stages using hand-sculpture tools, one applies successive layers of an initially malleable polyceramic material (such as the kind of material generally mentioned above), with an appropriate curing process conducted after each stage of build-up. This curing procedure involves placing of the structure in an appropriate chamber in a normal atmospheric pressure condition, and then using light (as from a halogen source) to cure the material to hardness. An appropriate number of build-up stages are employed to end up with an outer polyceramic jacket having substantially the final required outside topography of the intended tooth crown.

It is significant to note that silane layer 20 plays a key role in making practically possible the use of a high-temperature ceramic (aluminum oxide) core (which is easily and inexpensively "cementable" directly to a tooth preparation, or other reception structure), and an outside polyceramic jacket (which seals well to a tooth, and which offers excellent performance in the mouth without the necessity of performing a very time-consuming "bonding" procedure in the dentist's office). It does so in the intermediary layer-structure environment which includes (a) porcelain in the confronting interface with the core material, and (b) "bonding" adhesive in the interface with the jacket material.

Finally, an appropriate conventional glaze (layer 24 in FIG. 2) is brushed onto the outside surface of the polyceramic jacket. This glaze is cured in a pressurized, nitrogen-rich chamber utilizing the application of light as a curing mechanism. Thereafter, the emerging crown device is placed in a vacuum chamber for about 15-minutes at a temperature of about 200° F.

The device structure just disclosed herein clearly meets all of the objectives intended for it, in light of the issues mentioned earlier which relate to current dental prosthetic devices. Specifically, a device built in accordance with the present invention affords the opportunity for low-cost and easily performed "cementing" onto a tooth preparation in a patient's mouth, or onto some other kind of surface such as the two other kinds of tooth-preparation reception surfaces mentioned above. Additionally, the structure of the invention offers an environment for "bonding" joinery to take place between the core component and the jacketing component—a joinery approach which is preferred and very advantageous. The "bonding" interface does not need to be created by the dentist during an appointment with a patient, and accordingly, offers itself in the structure of the present invention in a way which is extremely cost-saving and economical. The presence of the intermediary layer structure, including the layers of porcelain, silane, and "bonding" adhesive, in the interface between the core and the jacket in a device built in accordance with this invention plays an important role in permitting the use of effective "bonding" in the region interposed the core and the jacket.

On another important point, with a device built in accordance with the present invention using the kinds of materials described for it in the core component and in the jacket component, those skilled in this art will recognize that this arrangement offers the dentist, dental technician, dental lab person, etc. a very flexible and wide-ranging opportunity for creating a device which is easily colored to look quite natural when installed in place in a patient's mouth.

Further talking a bit more about this coloration and aesthetics consideration, and how this relates to the use of "cementing" directly onto a tooth preparation, in the current state of the art, the only existing circumstance wherein a dentist can easily employ "cementing" as a technique for use in the office during an appointment with a patient, and in relation to installation of a prosthetic device such as a crown, is a situation wherein a crown has porcelain baked onto a metal core, which core, therefore, forms a structural interface between the jacket and the surface, for example, of a tooth preparation. In this specific kind of circumstance, the crown unit per se is thus formed of a combination of materials wherein the translucent jacket effectively telegraphs the dark, metallic appearance of the underlying core. Accordingly, color control is difficult to implement with any final character which makes the installed unit look natural. By promoting, in accordance with our invention, the use of a prosthetic device in which the outer jacket, our polyceramic jacket, seats effectively on an inner ceramic core, the telegraphing of unwanted color does not become an issue, inasmuch as the color of the underlying core material can easily be controlled. With this color-controllable condition thus present for the core material, fine-tuning of overall color control, through adjusting subtle coloration in the polyceramic jacketing material is very possible. In particular, it is possible in a setting wherein it is not necessary to have to consider "masking" the color of the core material. This core material, in addition, and in accordance with a major offering provided by our new invention, is one which permits the dentist confidently to use a cementing technique directly in the mouth of a patient.

As was mentioned earlier, the structure of the present invention can be employed in dental prosthetic devices other than crowns. Specifically, the structure proposed by this invention is readily usable in the context of a dental bridge, and FIG. 4 in the drawings generally illustrates this opportunity. Accordingly, and turning attention now specifically to FIG. 4, a dental bridge prepared in accordance with the present invention is shown generally at 28. This bridge includes a pair of crown-like units 30, 32, a beam 34 which spans and joins with these two units, and a pontic 36 which is anchored to structure 34 in the space between units 30, 32.

Each of units 30, 32 is formed in substantially the same manner, and with substantially the same end construction, described above herein in relation to crown 14. Each of these two crown-like units is joined to a tooth preparation, and two such tooth preparations are shown generally at 38, 40 in FIG. 4. Pontic 36 replicates a natural tooth in the space between crown-like units 30, 32.

While the invention has been disclosed in its preferred form, the specific embodiments thereof as disclosed and illustrated herein are not to be considered in a limiting sense, inasmuch as numerous variations are possible. The subject matter of the invention includes all novel and non-obvious combinations and subcombinations of the various elements, features, functions and/or properties disclosed herein. No single feature, function, element or property of the disclosed embodiments is essential. The following claims define certain combinations and subcombinations which are regarded as novel and non-obvious. Other combinations and subcombinations of features, functions, elements and/or properties may be claimed through amendment of the present claims or presentation of new claims in this or a related application. Such claims also are regarded as included within the subject matter of the present invention irrespective of whether they are broader, narrower, or equal in scope to the original claims.

It is desired to claim and secure by Letters Patent:

1. A dental prosthetic device adapted to be seated upon and anchored to an exposed tooth preparation comprising an inner core formed of a ceramic material, and an outer jacket joined to said core and formed of a polyceramic material.

2. The device of claim 1 which takes the form of a dental crown.

3. The device of claim 1 which takes the form of a dental bridge.

4. A dental prosthetic device adapted to be seated upon and anchored to an exposed tooth preparation comprising an inner core formed of a ceramic material, an outer jacket joined to said core and formed of polyceramic material, and layer structure, including silane, disposed intermediate said core and said jacket, and forming a joining interface between the two.

5. The device of claim 4, wherein said layer structure further includes a layer of porcelain disposed intermediate said silane and said core, and a layer of bonding agent disposed intermediate said silane and said jacket.

6. The device of claim 4 which takes the form of a dental crown.

7. The device of claim 4 which takes the form of a dental bridge.

8. A dental prosthetic device adapted to be seated upon and anchored to an exposed tooth preparation comprising an outer jacket formed of a polyceramic material and having an inside cavity, and joinder structure having an outside surface expanse that is joined by bonding to said jacket within its said inside cavity, and an inside cavity having an inside surface expanse which is joinable by cementing to such an exposed tooth preparation.

9. The device of claim 8, wherein said joinder structure includes an inner core unit formed of a ceramic material.

10. The device of claim 8, wherein said joinder structure includes a layer formed of silane.

11. The device of claim 8 or 9, wherein said joinder structure includes a core unit formed of a ceramic material, and a layer of silane formed on the outside surface of said core unit.

12. The device of claim 9, wherein said joinder structure includes a layer of silane which is disposed intermediate said jacket and said core unit.

13. The device of claim 8 which takes the form of a dental crown.

14. The device of claim 8 which takes the form of a dental bridge.

15. A dental prosthetic device adapted to be seated upon and anchored to an exposed tooth preparation which includes a base with an outside surface, a stump joined to and projecting from said base, and a shoulder extending between said base's said outside surface and said stump in the region of joinder between the two, said device comprising a core seatable essentially directly on such a stump, and including a lower extremity portion which, with the core seated on such a stump, resides in a condition spaced from the associated tooth-preparation shoulder, and a jacket anchored to the outside of said core, and including a lower extremity portion which, with the device in place on a tooth preparation, extends into the space existing between the tooth preparation's shoulder and the lower extremity portion of said core, and contacts the tooth preparation's stump in the vicinity of that space.

16. The device of claim 15, wherein, with the device in place on a tooth preparation, the space between the lower extremity portion of said core and the tooth preparation's shoulder, defines at least partially an endless, generally annular channel that circumsurrounds the tooth preparation's stump, and the lower extremity portion of said jacket substantially fills such channel.

17. The device of claim 15 which takes the form of a dental crown.

18. The device of claim 15 which takes the form of a dental bridge.

\* \* \* \* \*